US011259703B2

(12) United States Patent
Ghosh et al.

(10) Patent No.: US 11,259,703 B2
(45) Date of Patent: Mar. 1, 2022

(54) MICROSCOPY IMAGING DEVICE WITH ADVANCED IMAGING PROPERTIES

(71) Applicant: The Board of Trustees of the Leland Stanford Junior University, Stanford, CA (US)

(72) Inventors: Kunal Ghosh, San Francisco, CA (US); Laurie D. Burns, Menlo Park, CA (US); Abbas El Gamal, Palo Alto, CA (US); Mark J. Schnitzer, Palo Alto, CA (US); Eric Cocker, Palo Alto, CA (US); Tatt Wei Ho, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/080,295

(22) Filed: Oct. 26, 2020

(65) Prior Publication Data

US 2021/0267458 A1 Sep. 2, 2021

Related U.S. Application Data

(63) Continuation of application No. 15/444,049, filed on Feb. 27, 2017, now Pat. No. 10,813,552, which is a
(Continued)

(51) Int. Cl.
*A61B 5/00* (2006.01)
*G02B 21/00* (2006.01)
(Continued)

(52) U.S. Cl.
CPC ............ *A61B 5/0071* (2013.01); *A61B 90/20* (2016.02); *G01N 21/6458* (2013.01);
(Continued)

(58) Field of Classification Search
CPC ... A61B 5/0071; A61B 5/0042; A61B 5/0082; A61B 5/489; A61B 90/20;
(Continued)

(56) References Cited

U.S. PATENT DOCUMENTS 6,154,282 A 11/2000 Lilge et al.
2004/0227087 A1* 11/2004 Markham .......... G01N 21/3504
250/339.08
(Continued)

FOREIGN PATENT DOCUMENTS

WO 2008024080 A1 2/2008
WO 2009088930 A2 7/2009

OTHER PUBLICATIONS

EPO. European Examination Report dated Nov. 23, 2021, for related European Patent Application No. 17194462.2 of the common Applicant, 6 pages.
(Continued)

*Primary Examiner* — Allen C Wong
(74) *Attorney, Agent, or Firm* — Crawford Maunu PLLC

(57) ABSTRACT

Systems, methods and devices are implemented for microscope imaging solutions. One embodiment of the present disclosure is directed toward an epifluorescence microscope. The microscope includes an image capture circuit including an array of optical sensor. An optical arrangement is configured to direct excitation light of less than about 1 mW to a target object in a field of view of that is at least 0.5 mm$^2$ and to direct epi-fluorescence emission caused by the excitation light to the array of optical sensors. The optical arrangement and array of optical sensors are each sufficiently close to the target object to provide at least 2.5 μm resolution for an image of the field of view.

1 Claim, 6 Drawing Sheets

Related U.S. Application Data continuation of application No. 14/857,156, filed on Sep. 17, 2015, now Pat. No. 9,629,554, which is a continuation of application No. 13/218,181, filed on Aug. 25, 2011, now Pat. No. 9,195,043.

(60) Provisional application No. 61/377,591, filed on Aug. 27, 2010.

(51) Int. Cl.

| | |
|---|---|
| *G01N 21/64* | (2006.01) |
| *G02B 21/36* | (2006.01) |
| *G02B 21/16* | (2006.01) |
| *A61B 90/20* | (2016.01) |
| *G02B 3/00* | (2006.01) |
| *G02B 27/14* | (2006.01) |
| *G06T 7/00* | (2017.01) |
| *H04N 5/225* | (2006.01) |
| *H04N 5/232* | (2006.01) |
| *A61B 90/30* | (2016.01) |

(52) U.S. Cl.
CPC .......... *G02B 3/0087* (2013.01); *G02B 21/008* (2013.01); *G02B 21/0008* (2013.01); *G02B 21/16* (2013.01); *G02B 21/36* (2013.01); *G02B 21/361* (2013.01); *G02B 21/362* (2013.01); *G02B 21/365* (2013.01); *G02B 27/141* (2013.01); *G06T 7/0012* (2013.01); *H04N 5/2254* (2013.01); *H04N 5/2256* (2013.01); *H04N 5/23296* (2013.01); *A61B 5/0042* (2013.01); *A61B 5/0082* (2013.01); *A61B 5/489* (2013.01); *A61B 2090/306* (2016.02); *A61B 2503/40* (2013.01); *A61B 2503/42* (2013.01); *A61B 2562/0233* (2013.01); *A61B 2562/04* (2013.01); *A61B 2576/026* (2013.01); *G06T 2207/30016* (2013.01); *G06T 2207/30101* (2013.01)

(58) Field of Classification Search
CPC .......... A61B 2090/306; A61B 2503/40; A61B 2503/42; A61B 2562/0233; A61B 2562/04; A61B 2576/026; G01N 21/6458; G02B 3/0087; G02B 21/0008; G02B 21/008; G02B 21/16; G02B 21/36; G02B 21/361; G02B 21/362; G02B 21/365; G02B 27/141; G06T 7/0012; G06T 2207/30016; G06T 2207/30101; H04N 5/2254; H04N 5/2256; H04N 5/23296
USPC .......................................................... 348/80
See application file for complete search history.

(56) References Cited

U.S. PATENT DOCUMENTS

| | | | |
|---|---|---|---|
| 2006/0192081 A1* | 8/2006 | Cartlidge | G02B 27/0012 250/208.1 |
| 2008/0204551 A1 | 8/2008 | O'Connell et al. | |
| 2010/0165188 A1* | 7/2010 | Jannard | H04N 5/23241 348/375 |
| 2010/0208054 A1 | 8/2010 | Farr | |
| 2010/0315708 A1* | 12/2010 | Amberger | G02B 21/06 359/389 |

OTHER PUBLICATIONS

Mudanyali, Onur et al. "Compact, light-weight and cost-effective microscope based on lensless incoherent holography for telemedicine applications." Lab on a Chip, vol. 10, No. 11, Jan. 1, 2010, pp. 1417-1428.

Flusberg, et al. "In vivo brain imaging using a portable 3.9 gram two-photon fluorescence microendoscope." Opt Lett., Sep. 1, 2005; 30(17): 2272-4.

* cited by examiner

MICROSCOPY IMAGING DEVICE WITH ADVANCED IMAGING PROPERTIES

FEDERALLY-SPONSORED RESEARCH AND DEVELOPMENT

This invention was made with Government support under contract DE-A52-07NA27344 awarded by the Department of Energy. The Government has certain rights in this invention.

OVERVIEW OF CERTAIN EMBODIMENTS

Aspects of the present disclosure relate generally to microscopy imaging devices, for example, miniature epifluorescence imaging devices.

Optical microscopes are often designed as instruments of substantial size and expense. The role of imaging in biomedicine has grown, and miniaturized integration of the light microscope facilitates the advancement of many new applications. For instance, mass-producible, tiny microscopes, can be useful for imaging of cells in freely behaving animals, and particularly in the brain, for which is useful for understanding how cellular dynamics relate to animal behavior.

Although not limited thereto, aspects of the present disclosure relate to miniature (<2 g), integrated fluorescence microscopes made from mass-producible parts, including a semiconductor light source and image sensor, allowing imaging across ~0.5 $mm^2$ areas. Such devices can be configured for high-speed observation of cellular dynamics with sufficient image quality and/or resolution that such observation is useful for viewing dynamics of the brains of active mice at frame acquisition rates up to 100 Hz. The use of a miniature microscope can be useful for a variety of different applications (e.g., tracking Ca2+-spiking concurrently in up to >200 Purkinje neurons extending over 9 cerebellar microzones).

Aspects of the present disclosure are directed toward epifluorescence microscopes. The microscope includes an image capture circuit with an array of optical sensors. An optical arrangement is configured to direct excitation light of less than about 1 mW to a target object in a field of view that is at least 0.5 $mm^2$ and to direct epi-fluorescence emission caused by the excitation light to the array of optical sensors. The optical arrangement and array of optical sensors are each sufficiently close to the target object to provide at least 2.5 µm resolution for an image of the field of view.

Certain embodiments of the present disclosure are directed to an epifluorescence microscope that has an optical light source configured to produce excitation light from an energy source that provides less than 6 mW. The microscope includes an imaging circuit including a sensor array and an objective lens configured to operate sufficiently close to the optical light source, the image sensor array and to a target object to provide at least 2.5 µm image resolution for the field of view that is at least 0.5 $mm^2$.

Other embodiments of the present disclosure relate to epifluorescence microscopes that occupy less than a cubic inch. Such a microscope includes an optical excitation arrangement configured to direct light toward a field of view containing an imaging target. An imaging circuit including optical sensor array is configured to generate image data from fluorescence caused by an interaction between the directed light and the imaging target. An optical arrangement is configured to direct the fluorescence to the optical sensor array with sufficient intensity and focus for the image data to depict over 0.20 $mm^2$ and a resolution of at least 3 µm. In other embodiments the intensity and focus for the image data is sufficient to depict at least 2.5 µm image resolution for the field of view that is at least 0.5 $mm^2$ Consistent with other embodiments of the present disclosure, an imaging device includes a portable housing that is less than a cubic inch in size. The portable housing contains several elements including an excitation source configured to provide excitation light. A structure is also included, the structure being configured to provide an optical pathway having a first end and a second end. The structure includes an objective lens at the first end of the optical pathway; one or more excitation elements that are configured and arranged to direct the excitation light to the objective lens; and one or more emission elements that are configured and arranged to provide a focal plane at the second end of the optical pathway from epifluorescent emission light received from the objective lens. An imaging circuit includes an array of optical sensors positioned at the focal plane and configured and arranged to capture an image of the target object from the epifluorescent emission light, the image having sufficient field of view to capture multiple individual capillary blood vessels and sufficient resolution to distinguish the individual capillary blood vessels from one another.

Certain aspects of the present disclosure are exemplified in a number of illustrated implementations and applications, some of which are shown in the figures and characterized in the claims section that follows. The above overview is not intended to describe each illustrated embodiment or every implementation of the present disclosure.

BRIEF DESCRIPTION OF THE DRAWINGS

Aspects of the present disclosure may be more completely understood in consideration of the detailed description of various embodiments of the present disclosure that follows in connection with the accompanying drawings, in which.

Figure 1:
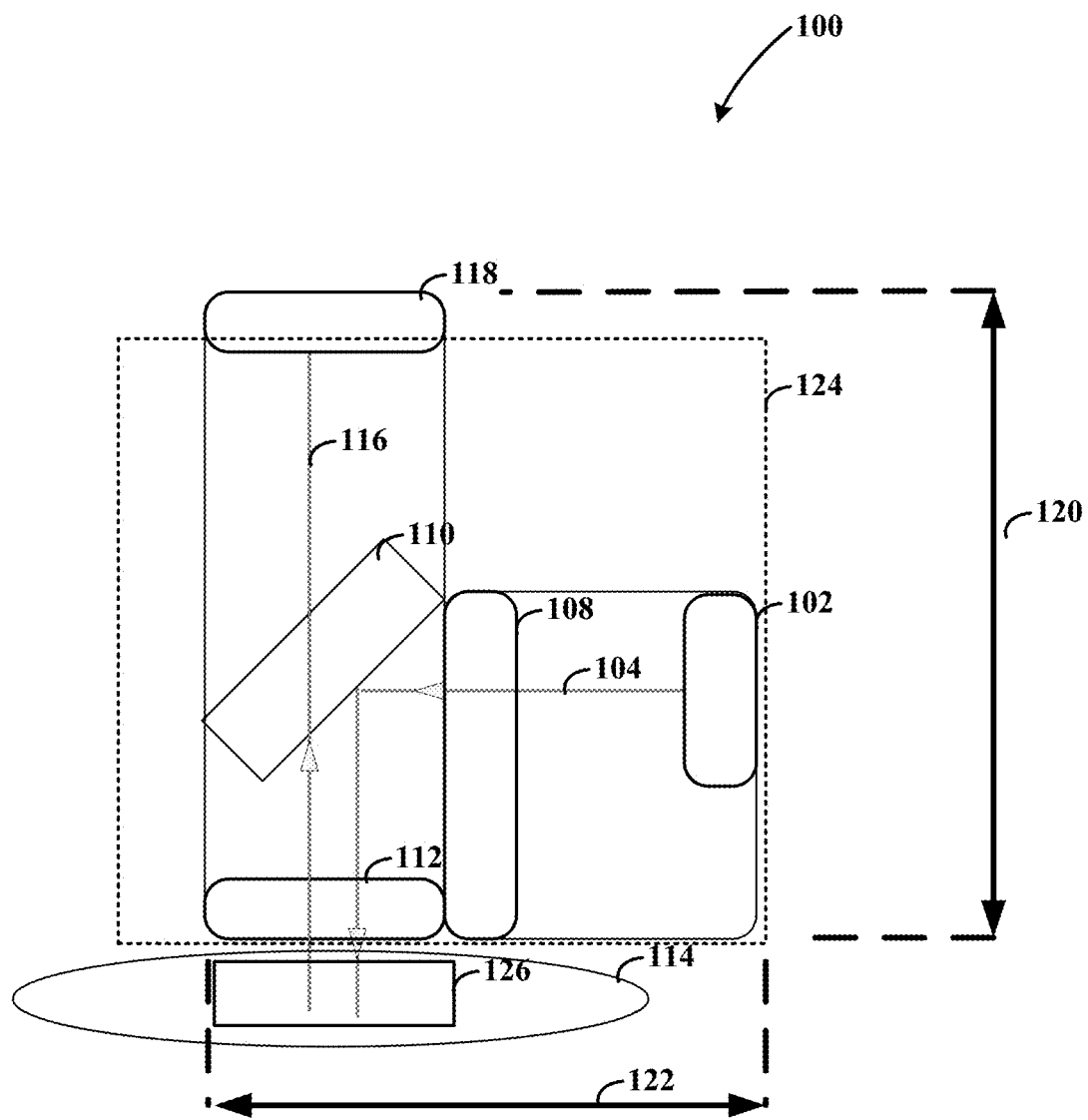
FIG. 1 depicts a block diagram of an epifluorescence microscope device, consistent with an embodiment of the present disclosure.

While the present disclosure is amenable to various modifications and alternative forms, specifics thereof have been shown by way of example in the drawings and will be described in further detail. It should be understood, however, that the intention is not to limit the disclosure to the particular embodiments described. On the contrary, the intention is to cover all modifications, equivalents, and alternatives falling within the spirit and scope of the present disclosure.

DETAILED DESCRIPTION

The present disclosure is believed to be applicable to a variety of different types of devices and processes, and the present disclosure has been found to be particularly suited for epifluorescent imaging applications. While the present disclosure is not necessarily limited to such applications, various aspects of the present disclosure may be appreciated through a discussion of various examples using this context.

Consistent with certain example embodiments of the present disclosure, epifluorescent imaging is facilitated through the use of a microscope device and system. For instance, particular aspects of the device and/or system allow the use of ultra-low levels for excitation light, which are used to generate epi-fluorescence in a target object or cell. Some aspects allow for imaging of a large field of view with a high resolution. Still further aspects are directed toward the high-speed capture of images, which can be viewed in real-time or near real-time. While these points of facilitation are not limiting, they are relevant to a number of different embodiments of the present disclosure.

A particular aspect relates to the proximity between an optical source of excitation light and the target object or cell for imaging. For epifluorescent imaging, the interaction between the excitation light and the target object causes the generation of imaging fluorescence. The excitation light is directed toward the target object and has a specific wavelength configured for absorption by fluorophores, fluorescent markers or fluorescent probes. The fluorophores then emit light at different (e.g., longer) wavelengths. The amount of absorbed light is related to the amount of excitation light delivered to the target object. In this manner, the amount of fluorescence generated is correlated to the amount of excitation light. Although various light delivery mechanisms can help reduce the attenuation of light as it travels through a medium, the attenuation of light will increase as distance of travel through a medium increases. Also, when using air and other mediums, the composition of the medium and other dispersive attributes can play significant roles in the delivery and/or attenuation of the light, whereas the reduction of the optical path length (mainly resulting in the reduction of travel of light through air) does next to nothing to decrease attenuation. The design of the microscope device and system allows for the placement of the optical source of the excitation light in close proximity to the target object, thereby facilitating the use of a short optical path. This is particularly useful for facilitating the use of an optical source of low power and/or capturing images using low-levels of light.

Various fluorescence sources can be used consistent with one or more embodiments discussed herein. The mention of a particular source of fluorescence does not necessarily preclude use of other sources of fluorescence (e.g., genetically-encoded fluorescent proteins, such as GFP, GCaMP, and variants thereof).

Other aspects of the present disclosure relate to the integration of optics, filters, and camera into a single housing, which can be particularly useful for the elimination of the fiber-bundle and all of its associated limitations.

Yet other aspects relate to the proximity of a target object or cell relative to an image sensor for capturing image data from epifluorescent light. Image resolution and imaging times are related to the amount of epifluorescent light that can be collected and detected by an image sensor. Attenuation of the epifluorescent light due to properties of the optical path between the target object and the image sensor can be undesirable. Careful design of the microscope device and system allows for placement of the image sensor in close proximity to the target object, thereby facilitating the use of a short optical path.

Also in accordance with the present disclosure, the proximity of an objective lens of a microscope device is set relative to a target object, during imaging of the target object. Large distances between an objective lens and the target object can have a detrimental effect on the amount of the excitation light received at the target object as well as the amount of fluorescence received at and collected by the objective lens. Accordingly, setting the proximity of the object lens relative to the target object can be advantageous.

Embodiments of the present disclosure relate to a microscope device and system that captures image data for a relatively large field of view, the image data providing high resolution of a target object. One such embodiment of the present disclosure includes an image capture circuit, with an array of sensor elements or pixels, which is provided to image the field of view. The sensor elements detect epifluorescence for different portions of the field of view. The sensor elements can be configured with sufficient sensitivity and proximity to the target object to facilitate image capture and generation.

Other embodiments of the present disclosure relate to the length of exposure times for image capture. As fluorophores are excited, they can begin to lose their ability to fluoresce, which is sometimes referred to as photobleaching. Moreover, epi-fluorescence imaging involves the absorption of the excitation light by the target object. Some of this absorbed light is converted into heat. This generated heat can place limits on the exposure time, e.g., the heating of biological material/cells can cause cell damage and even death. The exposure time, however, can be increased if the intensity of excitation light is decreased. The intensity of the excitation light can be reduced if, for example, the optical coupling between the target object and the image sensor is improved. Phototoxic effects can be more damaging than localized heating. Aspects of the present disclosure lessen or eliminate these effects which adversely impact image capture and related processing of the data.

Particular embodiments of the present disclosure relate to the adjustment of excitation light intensity in conjunction with the adjustment of exposure time to improve image quality, or an image for a particular goal (e.g., image capture rate, resolution, field of view size or imaging depth).

According to other aspects of the present disclosure, relatively low optical zooms are used in connection with high-resolution imaging of a field of view for target objects of small size. Constraints on the optical zoom required for a particular level of imaging can be lessened through the careful design and application of a microscope device and system consistent with various aspects discussed herein.

Embodiments of the present disclosure relate to the real-time imaging of target objects using a microscope device and/or system consistent with aspects discussed herein. In certain of these embodiments, the imaging rate is increased by reducing the field of view while holding a constant resolution, the image capture time is reduced by reducing the exposure time and/or the frame rate achievable for such real-time imaging is correlated to size of the full field of view as well as the desired image resolution. Another factor optionally implemented therewith includes the type and responsiveness of the image sensor that is used. Still other factors relate to the ability to transmit and process the image data for display, should it be desirable to view the images in real-time.

Still other embodiments of the present disclosure relate to the facilitation of in vivo or in vitro epifluorescent imaging. For instance, in vivo imaging of a live subject can be particularly useful for correlating external stimuli and other factors with the captured images. This correlation can be used, for example, as a diagnostic/research tool by associating properties of the captured images with the external stimuli. Real-time imaging at high frame rates can further provide such correlation as a function of time.

An embodiment of the present disclosure is directed toward a microscope device and/or system having a modular design that facilitates detaching and reattaching various components of the microscope device. The detachment and reattachment can be used to replace the modular components with new and/or different modular components. For instance, the light source can be replaced with a new light source having the same or different optical and electrical properties. The array of optical sensors and/or the optical direction elements (e.g., mirrors, filters and lenses) can also be removed and replaced. If desired, the optical sensor can also be removed and replaced.

In certain other embodiments consistent with the instant disclosure, one or more of the imaging devices includes a synchronization circuit for interfacing to an external optical-data processing (recording and/or configuring) system. The synchronization circuit includes logic circuitry (e.g., a programmable or semi-programmable chip (microcontroller or ASIC) that is configured and arranged to communicate a frame reference/active signal. In a typical application, a frame active signal would provide synchronization information, e.g., as defined in an IEEE communications standard, for and with the data communicated between the imaging device and the external system. Such an optical-data recording/configuring system can be used to install software, configure set-up parameters for experiments and procedures, provide visual feedback during such experiments and procedures, and record the optical data for manipulation and further study.

In yet further embodiments, the instant disclosure is directed to methods of using the image devices which are described herein. Certain of the devices include a base plate acting as a foundational structure which provides support/stability and also allows for microscope (re)alignment. These methods include the steps of attaching and reattaching the epifluorescence microscope to the base plate for allowing the microscope alignment to be precise. Such precision should be sufficient for repeated imaging of a common imaging location, e.g., during chronic experiments.

Turning now to the figures, FIG. 1 depicts a block diagram of an epifluorescence microscope device, consistent with an embodiment of the present disclosure. The epifluorescence microscope device 100 includes a number of components within the dimensions 120 and 122. Not shown is a further dimension, which extends perpendicular to the dimensions 120 and 122. Although not necessarily limited thereto, each of these dimensions can be less than an inch. Consistent with other embodiments, the dimensions are slightly larger, e.g., on the order of a few centimeters.

The epifluorescence microscope device 100 includes an optical source 102. This optical source 102 generates excitation light 104. In a particular implementation, the optical source 102 is a light-emitting-diode (LED) or an organic light-emitting-diode (OLED). The excitation light 104 is directed by an optical arrangement 124 to a target object 114, for imaging thereof. The optical arrangement can include one or more of objective lens 112, (dichroic) mirror 110 and excitation filter 108 and an emission filter (not depicted). Epifluorescent light 116 from the target object 114 is directed from/by the objective lens to an image capture circuit 118. The epifluorescence microscope device 100 is configured to direct light from and capture image data for a field of view 126.

In various embodiments of the present disclosure, the microscope device 100 can also include one or more of an image-focusing optical element (e.g., an achromatic lens) and an emission filter. These and other elements can help control optical properties of the microscope device 100.

Consistent with one embodiment, the depicted elements are each integrated into a relatively small area, e.g., within a single housing having dimensions 120, 122. Such integration of the various components can be particularly useful for reducing the length of the optical pathway from the optical source 102 to the target object 114 and back to the image capture circuit 118. The reduction of this optical pathway can be part of the configuration parameters that facilitate a number of different properties and capabilities of the microscope device 100. For example, in certain embodiments the microscope can provide images with a resolution to 1 um for an imaging field of view of up to 1 mm$^2$ in area.

A particular example embodiment is configured with an array of optical sensors 118. An optical arrangement 124 is configured to direct excitation light 104 of less than about 1 mW (various embodiments provide for a higher excitation power, e.g., 100 mW) to a target object 114 in a field of view 126 of that is at least 0.5 mm$^2$ and to direct epi-fluorescence emission 116 caused by the excitation light 104 to the array of optical sensors 118. In various embodiments, the field of view 126 can be at least 1 mm$^2$. The optical arrangement 124 and array of optical sensors 118 each configured sufficiently close to the target object 114 to provide at least 2.5 μm resolution for an image of the field of view 126. In other embodiments, the optical arrangement 124 and array of optical sensors 118 can be configured to provide at least 1 μm resolution. In certain embodiments, the excitation optical power at the specimen is variable and can be in the range of 100 μW-100 mW, depending upon the particular configuration and imaging constraints.

Consistent with an embodiment of the present disclosure, the optical source 102 can deliver light of up to 37 lumens or 6 mW. It is not, however, necessarily a requirement that the optical source 102 provide light of such intensity. Moreover, the amount of light received by the target object is less than (relative to an attenuation factor) the amount of light provided by the optical source 102. For instance, the attenuation of one embodiment results in 6 mW at the light source corresponding to 1 mW excitation power delivered at the target object. Similarly, to deliver 100 mW of excitation power at the specimen the light source can be configured to provide up to 600 mW.

Figure 2:
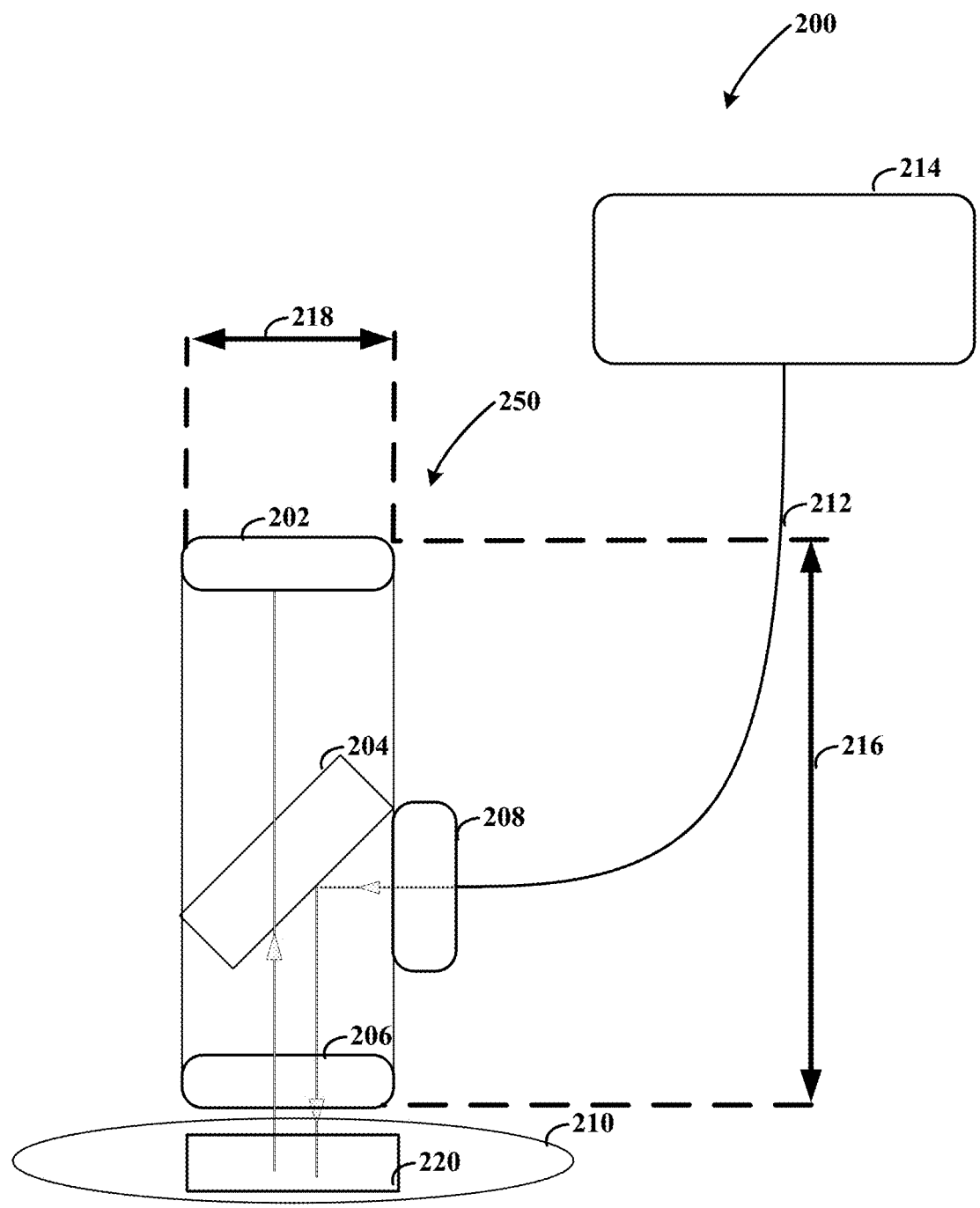
FIG. 2 depicts a block diagram of an epifluorescence microscope device with an external optical source, consistent with an embodiment of the present disclosure.

Although FIG. 1 depicts the various components as being within the dimensions 120, 122, other embodiments are possible. For instance, FIG. 2 depicts a block diagram of an epifluorescence microscope device with an external optical source, consistent with an embodiment of the present disclosure. The epifluorescence microscope device 200 includes an external optical source 214. This external optical source 214 is coupled to an optical arrangement 250 that includes a number of components within the dimensions 216 and 218. Not shown is a further dimension, which extends perpendicular to the dimensions 216 and 218. Although not necessarily limited thereto, each of these dimensions can be less than a cubic inch. Consistent with other embodiments, the dimensions are on the order of a few centimeters.

Consistent with one embodiment of the present disclosure, the external optical source 214 is coupled to the optical arrangement 250 via a fiber optic cable 212. Excitation light from the external optical source 214 and the fiber optic cable 212 pass through (optional) excitation filter 208. A (dichroic) mirror 204 and objective lens 206 direct the excitation light to the target object 210. In particular, the excitation light is directed toward field of view 220. The excitation light causes fluorophores in the target object 210 to fluoresce with epifluorescent light. This epifluorescent light is directed by (dichroic) mirror 204 and objective lens 206 to optical sensor 202.

In various embodiments of the present disclosure, the microscope device 200 can also include one or more of an image-focusing optical element (e.g., an achromatic lens) and an emission filter in the imaging pathway. These and other elements (not shown FIG. 1) can help control optical properties of the microscope device 200.

Although the optical source 214 is not located in close proximity to the optical arrangement 250, the amount of excitation light that is delivered to the target object 210 can still be set at a low level due to the proximity between the target object 210, the objective lens 206 and/or the optical sensor 202. In particular, this close proximity can be particularly useful for providing efficient optical coupling between the target object and the optical sensor. Thus, the epi-fluorescence can be of a lower intensity relative to the image properties. Moreover, a lower level of excitation intensity at the target object 210 can allow for longer exposure to the excitation light before photobleaching, heating or other adverse effects become a factor.

The following discussion provides details of an experimental embodiment. Although the experimental embodiment provides examples and details regarding various parameters and results, these aspects are not necessarily limiting to the various other embodiments of the present disclosure. The experimental embodiment was configured and arranged to provide a small epi-fluorescence microscope. The microscope included a specially-integrated arrangement that included the light source, optics, filters, and camera into a single housing.

The level of integration and the resulting size scale for the miniature fluorescence microscopes can be configured for use in a multitude of applications. A particularly challenging application relates to in vivo brain imaging, e.g., in a mouse or similar organism. In at least one such application, the microscope is designed to be mounted on the head of a mouse for in vivo brain imaging during awake behavior. In order to be configured for this and other applications, the microscope was designed with stringent physical size and mass requirements, e.g., so as to be easily borne by the mouse during awake and active behavior. For instance, given that an adult mouse is approximately 25 g in mass, the microscope was designed to be 3 g or less. Other design considerations revolved around the image quality, reliability and speed.

One embodiment was configured for imaging of high-speed, cellular-level brain imaging. The cost and simplicity of large-scale manufacturing was another factor in the design of the fluorescent microscope. Particular embodiments were configured and designed as an integrated device that was mass-producible at low costs (e.g., scalable and amenable to mass-production).

Figure 3:
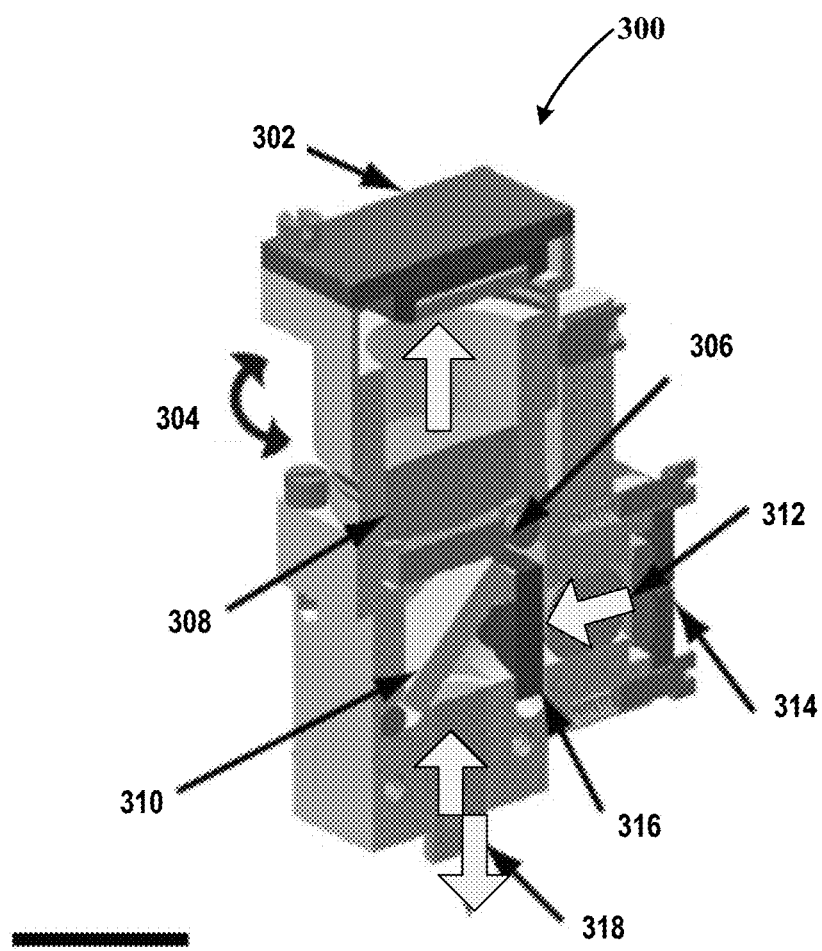
FIG. 3 shows a cross-section of a miniature fluorescence microscope, consistent with an embodiment of the present disclosure.

FIG. 3 shows a cross-section of a miniature fluorescence microscope that was designed consistent with such considerations and other embodiments of the present disclosure. The vertical arrows denote the excitation (down arrow) and emission (up arrow) pathways. A single housing 300 contains the light source 314 and image capture circuit 302, as well as a fluorescence filter set (emission filter 306 and excitation filter 316) and microoptics (collector lens 312, dichroic mirror 310, achromatic lens 308, objective lens 318 and focusing mechanism 304). This integration of the light source and camera with the filter set and microscope optics facilitates high-resolution image capture in various applications, such as in vivo imaging.

Consistent with one embodiment, a solid-state light-emitting-diode (LED), which is small, amenable to integration with collection optics, and mass-producible at low costs, is used for the excitation light source. A Complementary-Metal-Oxide-Semiconductor (CMOS) image sensor is used for the camera.

In a particular experimental embodiment of the present disclosure, the LED light source shown in FIG. 3 can be implemented using a blue LED 314 mounted on a custom 6 mm×6 mm printed circuit board (PCB), which also includes a heatsink. A drum micro-lens 312 is used to collect illumination, which then passes through a 4 mm×4 mm excitation filter 316, deflects off a dichroic mirror 310, and enters the imaging pathway. A gradient refractive index (GRIN) objective micro-lens 318 focuses illumination onto the sample. Fluorescence emissions from the sample return through the objective 318, the dichroic 310, a 4 mm×4 mm emission filter 306, and an achromatic doublet tube lens 308 that focuses the image onto the CMOS image sensor 302 (640× 480 pixels), mounted on a 8.4 mm×8.4 mm PCB with power and signal conditioning electronics. The LED light source, CMOS camera, and the optical components are integrated into a microscope housing 300 with a modular design that permits individual components, such as the excitation LED and CMOS camera chip, to be replaced for different application needs. Moreover, a memory circuit can be integrated to store image data. The modular aspect allows the memory circuit to be removed and replaced without removing the microscope from the imaging target (e.g., the microscope could remain affixed to an organism). Thus, captured images are stored locally and then retrieved by removal of the memory circuit, which can be configured to interface with an external device, such as a laptop computer.

In example embodiments, the microscope housing is fabricated using Polyetheretherketone (PEEK) and has built-in mechanical image focusing capabilities permitting focusing to sub-micron accuracy by adjustment of the camera position. Other materials (e.g., bio-compatible and solvent-resistant materials) can also be used consistent with various desired applications. The microscope can be plugged into a computer via external data acquisition PCBs, with a standard USB interface, providing real-time image acquisition, display, and camera and light source control.

Embodiments of the present disclosure are directed toward the design and control over an imaging pathway and design of an epifluorescence microscope. The imaging pathway includes an objective lens along with other optical conditioning and directing components. The additional components can include, for example, spectral-filtering components and/or an achromatic doublet imaging tube lens.

Figure 4:
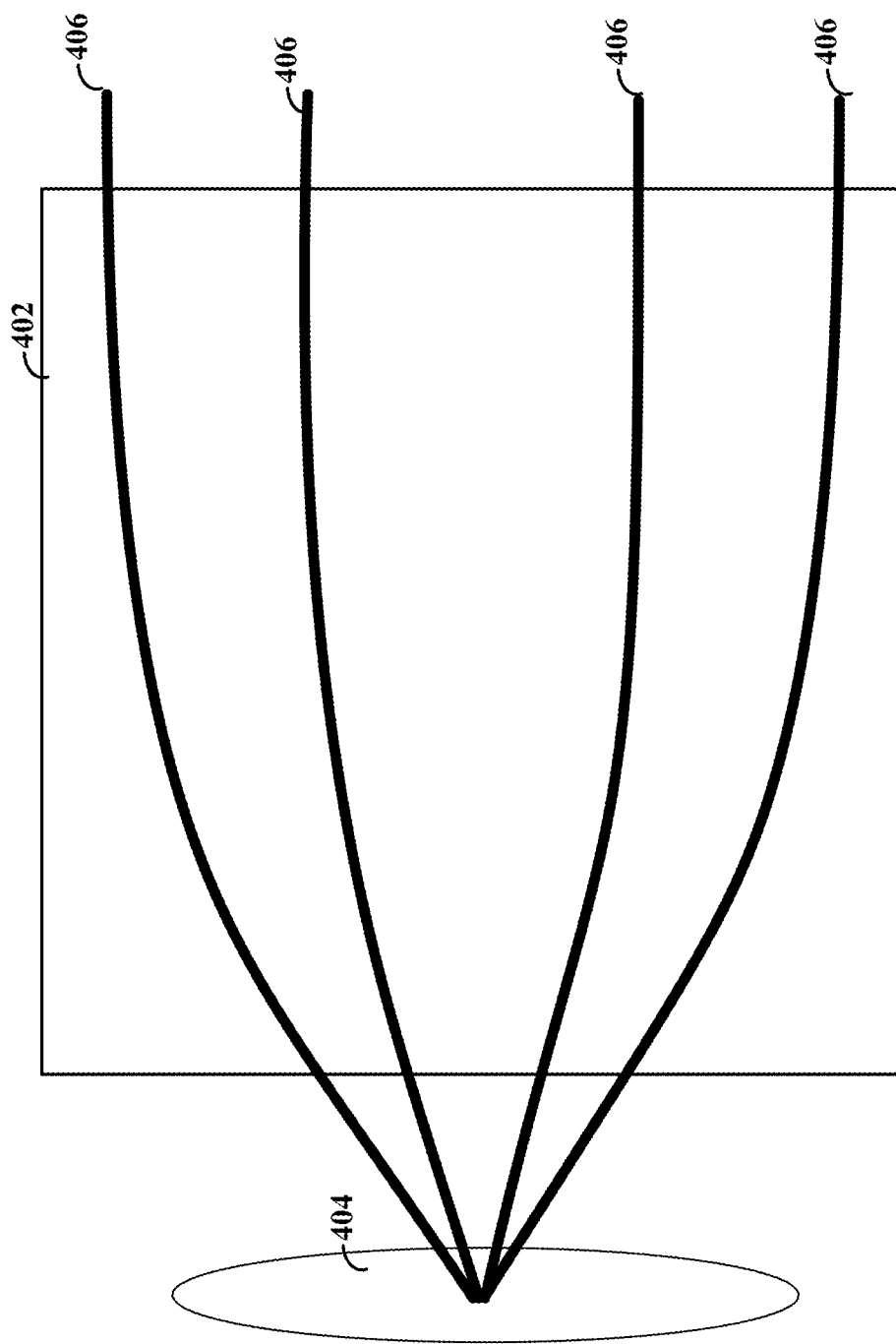
FIG. 4 depicts an objective lens and ray propagation therein, consistent with an embodiment of the present disclosure.

FIG. 4 depicts an objective lens and ray propagation therein, consistent with an embodiment of the present disclosure. In a particular embodiment, the objective lens 402 is a GRIN objective lens. The GRIN objective lens is a cylindrical lens with a radially-decreasing refractive index profile that results in rays 406, originating from target object 404, propagating in a sinusoidal path, as shown in FIG. 4. A GRIN lens can be particularly useful due to the small form factor and ease-of-integration with other microoptics and/or for reducing optical path length relative to other types of objective lenses.

In one experimental embodiment of the present disclosure, the GRIN objective lens used to collect fluorescence emission from the specimen is 2 mm in diameter with a pitch length of 0.245. A pitch length of 1 corresponds to one full sinusoidal path of ray propagation; thus a pitch length of 0.245 results in light rays that are close to being considered collimated light rays, as shown in FIG. 4. The objective numerical aperture (NA) is 0.45. Collected fluorescence emission is passed through the dichroic mirror and the miniature emission filter, and the fluorescence image is then focused by an achromatic lens, with a focal length of 15 mm, onto the CMOS image sensor.

Figure 5:
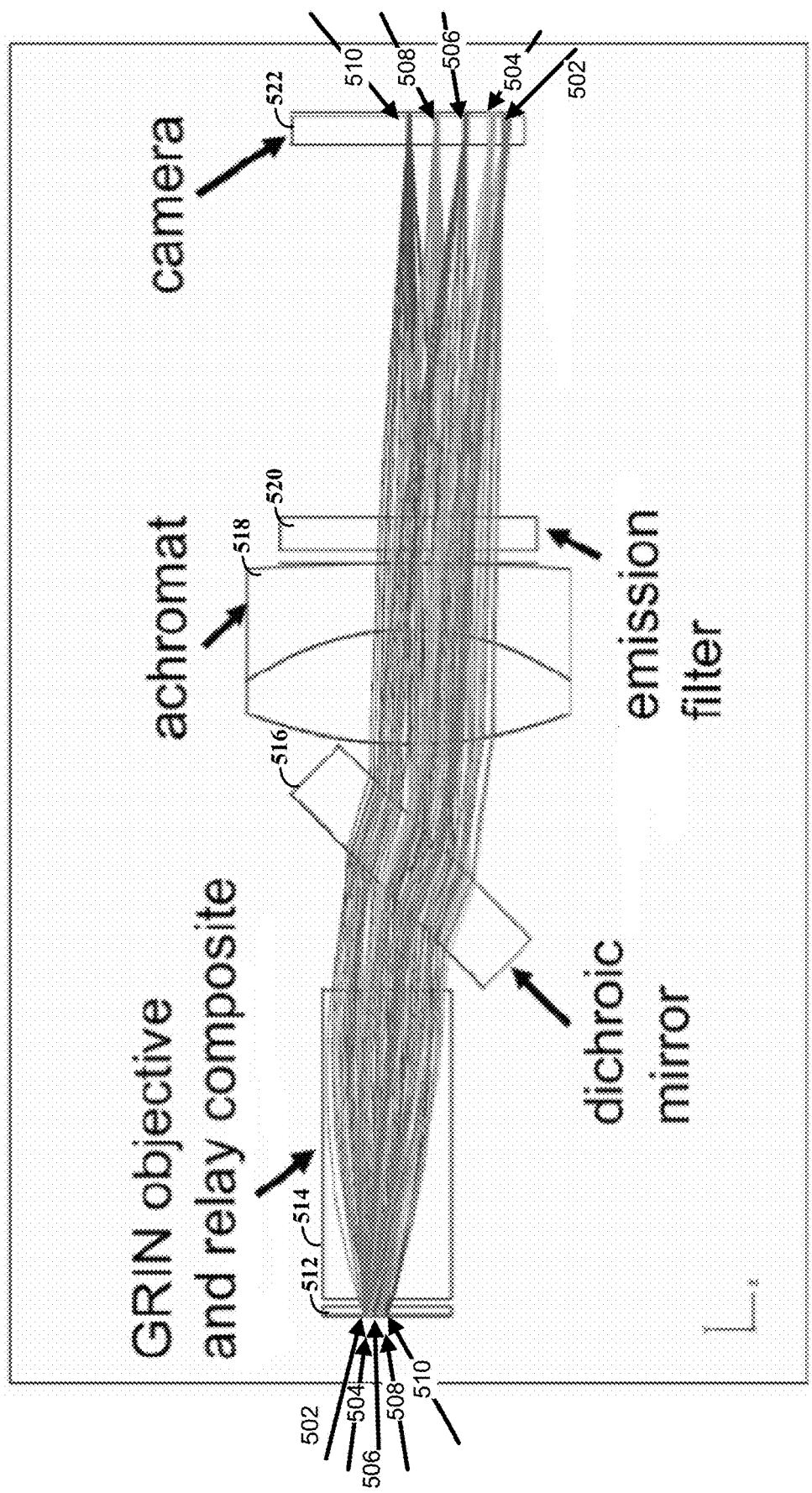
FIG. 5 depicts an optical ray trace diagram of an imaging pathway with two lens elements and an additional spectral-filtering components, consistent with an embodiment of the present disclosure.

FIG. 5 depicts an optical ray trace diagram of an imaging pathway with the two lens elements and the additional spectral-filtering components, consistent with an embodiment of the present disclosure. The rays show how points in the specimen plane are imaged onto the CMOS camera. Light rays (502, 504, 506, 508, 510) are traced from five distinct point sources in the specimen plane to imaged points on the CMOS camera. The design of the imaging pathway and the optical ray trace simulations were performed using software modeling. The light rays emanating from target object 512 pass through the GRIN objective lens 514. The GRIN objective lens 514 collimates the light rays. The light rays are then directed by dichroic mirror 516 toward achromatic lens 518. Emission filter 520 filters out undesired light wavelengths, such as reflected excitation light. The light rays then strike sensor array/camera 522, where they are recorded and used to generate an image of the target object 512.

The optical magnification provided by the imaging pathway and optical elements can be configured accordingly to the desired application. Moreover, the need for optical magnification can be offset by the proximity of the objective lens to the target object as well as the proximity between the target object, objective lens and the image capture circuit, resulting in embodiments where low optical magnifications (1-4×) can permit imaging large specimen fields-of-view greater than 1 mm$^2$ while still providing high spatial resolution of at least 1 μm.

Consistent with experiments and related embodiments, the microscope optical magnification range is between 4.5-5.5×. The working distance, that is, the distance from the near surface of the objective to the point in the specimen plane that is in focus, is about 150-200 μm or about 50-250 μm (these dimensions can depend on the exact positioning of the focal plane). The performance of an optical design can be evaluated by its resolving capabilities, and one measure of this is the full-width-half-maximum (FWHM) of the optical point-spread function. The on-axis, lateral spatial resolution of the imaging pathway computed in this manner was approximately 1.2 degrading to approximately 1.6 μm at the periphery of the field-of-view. This measurement, however, is not necessarily limiting as the spatial resolution achievable is also a function of various factors including, but not limited to, the camera pixel size.

Aspects of the present disclosure relate to properties of the illumination pathway between the target object, the excitation source and the image sensors. For instance, careful design of the illumination pathway can provide efficient and uniform excitation of the specimen under observation. The coupling of the excitation light source to the illumination pathway can be useful for providing sufficient and well-controlled illumination to excite the specimen. In one experimental implementation, a blue LED with the spectral peak of illumination at around 470 nm was used as the excitation light source. The LED was mounted on a 6 mm×6 mm PCB that was equipped with a heat sink. The heat sink helps to keep the LED junction temperature stable during operation.

LED illumination output is (first order) linear as compared with drive current only over a local area (the actual transfer function is a curve). However, the output exhibits temperature dependence. The experimental results showed that drive currents of 20-30 mA were sufficient to deliver the required illumination power at the specimen. This drive current was approximately one fiftieth (1/50) of the maximum rating for the drive current of the LED (e.g., maximum drive current is 1 A and typical drive currents are 20 mA). For a given drive current, the LED junction generally reached an equilibrium temperature in approximately 60 s after LED turn-on, and the LED illumination output stabilized. In certain embodiments, the LED light output can be stabilized in real-time over temperature variations via intrinsic or external temperature measurement coupled with a feed-forward or feedback system. For instance, data received from a temperature sensor (e.g., temperature sensitive resistor or temperature sensing diode) and/or current sensor can be used to control the amount of electrical power provided to the LED. In certain embodiments, a control circuit for providing such control can be calibrated during manufacturing or at a point thereafter.

Consistent with an experimental embodiment, the LED illumination is collected by a drum lens, passed through a miniature fluorescence excitation filter, and then reflected off a dichroic mirror that directs the illumination into the GRIN objective lens and to the specimen. The system was designed for collection and delivery of light to the specimen to achieve spatially uniform, homogenous illumination at an average optical power density across the specimen field-of-view. This can be accomplished by approximating Kohler illumination. In Kohler illumination, the light source and the specimen planes are on separate sets of conjugate planes, ensuring that the light source is not imaged onto the specimen, and yielding even illumination of the specimen at an average optical power density.

According to an experimental embodiment, the fluorescence filter set is configured to separate the excitation illumination from the fluorescence emission. The filter set includes three parts: the excitation filter, dichroic mirror, and emission filter. The spectral profiles of the filters and dichroic were configured to allow blue excitation and green emission. These spectral profiles are amenable to imaging a broad palette of synthetic fluorescent probes, such as fluorescein and its reactive derivatives, as well as genetically-encoded fluorescent proteins, such as the green fluorescent protein (GFP). For a particular experimental implementation, the specific spectral characteristics and dimensions of the filter set were as follows. The excitation filter was a bandpass filter with a spectrum of 480/40 nm and a dimension of 4 mm×4 mm×1.05 mm, the emission filter was also a bandpass filter with a spectrum of 535/50 nm and a similar dimension of 4 mm×4 mm×1.05 mm, and the dichroic mirror had a long pass spectral profile, passing wavelengths above 506 nm, and with a dimension of 4 mm×4.8 mm×1.05 mm. In other embodiments, the filter set can be configured to permit multiple wavelength excitation for excitation and imaging of multiple fluorescent markers with different excitation/emission spectra.

Embodiments of the present disclosure are directed toward the use of a CMOS image sensor. CMOS image sensors are digital imaging sensors that are designed and fabricated in CMOS. This can be particularly useful for providing image sensors that can be mass-produced at low costs. Moreover, the use of CMOS technology can be useful for providing a solution that operates at both low power and at high speed. The CMOS image sensors can be implemented with digital pixels, where conversion from photons to bits is done directly at the pixel level with a per-pixel analog-to-digital converter and dynamic memory. This can be particularly useful for high speed imaging applications and the implementation of still and video rate imaging applications that benefit from high-speed capture, such as dynamic range enhancement.

In a particular implementation a CMOS image sensor was used that had a resolution of 640×480 pixels, each pixel having dimensions of 5.6 μm×5.6 μm. The CMOS image sensor was packaged in a 5.6 mm×5.8 mm chip-scale package. The sensor output was in a serialized digital low-voltage differential signaling (LVDS) format. Such a LVDS format is particularly useful for facilitating the interfacing with a minimum number of interconnects, which can be an important consideration for minimizing the number of wires attached to the microscope.

Experimental characterizations, shown in table 1, of the sensor are briefly described as follows. Pixel read noise was estimated by calculating the standard deviation of pixel intensity in 1000 image frames, acquired in full darkness and with sufficiently brief exposure such that the noise contribution from dark current shot noise was insignificant. Dark current, and dark signal non-uniformity (DSNU), the variation in dark current across the array of pixels due to device mismatches, were estimated by capturing 1000 frames in the dark with sufficiently long exposure times, and then averaging the frames into a single image, with the objective of ideally averaging out temporal noise. Dark current and dark signal non-uniformity were then found from the mean and standard deviation of the pixels in the averaged image. With these experimentally-characterized sensor specifications, and other known electronic properties of the sensor, the CMOS image sensor was analytically modeled to estimate imaging fidelity for a range of incident photon flux densities.

TABLE 1

| Package size | 5.6 × 5.8 mm$^2$ |
|---|---|
| Array size | 640 × 480 pixels |
| Pixel size | 5.6 × 5.6 μm$^2$ |
| Frame rate | 36 fps/Hz |
| Pixel read noise | 10 e$^-$ |
| Dark current (room temp.) | 900 e$^-$/s |
| Dark signal non-uniformity | 30 e$^-$/s |
| Full well capacity | 52,000 e$^-$ |

The experimental results are illustrative and not meant to be limiting. For instance, the frame rate/image capture speed of Table 1 (36 Hz) is to be understood in the context of the specific experimental parameters. For instance, the captured field of view (FOV) was at least 0.5 mm$^2$, although it could be up to 1 mm$^2$ or even more. Smaller FOVs would allow for higher frame rates (e.g., 370 μm 370 μm at 100 Hz).

One application consistent with embodiments of the present disclosure relates to in vivo mouse brain imaging experiments. Since photon flux densities incident on the sensor plane for typical in vivo mouse brain imaging experiments are on the order of 10$^{11}$ photons/cm$^2$/sec, which corresponds to 20,000 electrons/pixel/sec, the CMOS image sensor operates in the photon shot noise limited regime for in vivo mouse brain imaging experiments. Thus, the CMOS image sensor's pixel read noise and dark current numbers, relevant considerations for applications where imaging is performed in low-light conditions, have a negligible impact on imaging fidelity. Along with an estimated sensor dynamic range of 60 dB, which is believed to be more than sufficient for capturing the range of signal intensities observed in in vivo brain imaging datasets, the imaging performance metrics of the CMOS image sensor were shown to be well-suited to serving the application needs.

Embodiments of the present disclosure relate to communication of image data, control signals and/or power to the microscope device. For many applications, the intrusiveness of the microscope is a relevant consideration. This aspect can be adversely affected by the number of wires used to provide the communication and/or power to the microscope device. Accordingly, various aspects of the present disclosure are directed toward reducing the number of wires between the microscope and an external system, which can provide control and/or image storage and processing functions. Consistent with a particular experimental implementation, a two-wire I2C interface is used to communicate control information with the microscope device. The I2C interface defines the wires as SCLK and SDATA and communicates using a serial interface, thereby providing a low wire count solution. In certain embodiments, an additional rotational element (e.g., commutator) can be used to facilitate movement and to lessen or eliminate torsional strain on the connection wires. Various other protocols and communication solutions are possible.

Consistent with a particular embodiment of the present disclosure, the input power supply is stepped-down and regulated by a low-dropout voltage regulator (LDO) before being delivered to the image sensor. An input clock signal (162 MHz) is transmitted to and restored by a clock buffer before being sent to the image sensor. The received clock signal is then used to internally generate a 27 MHz master clock signal. The image data output of the sensor is in a 10-bit digitized format and transmitted over a two-wire serial LVDS protocol. The present disclosure, however, is not necessarily limited to any particular communication protocol or power providing mechanism.

Figure 6:
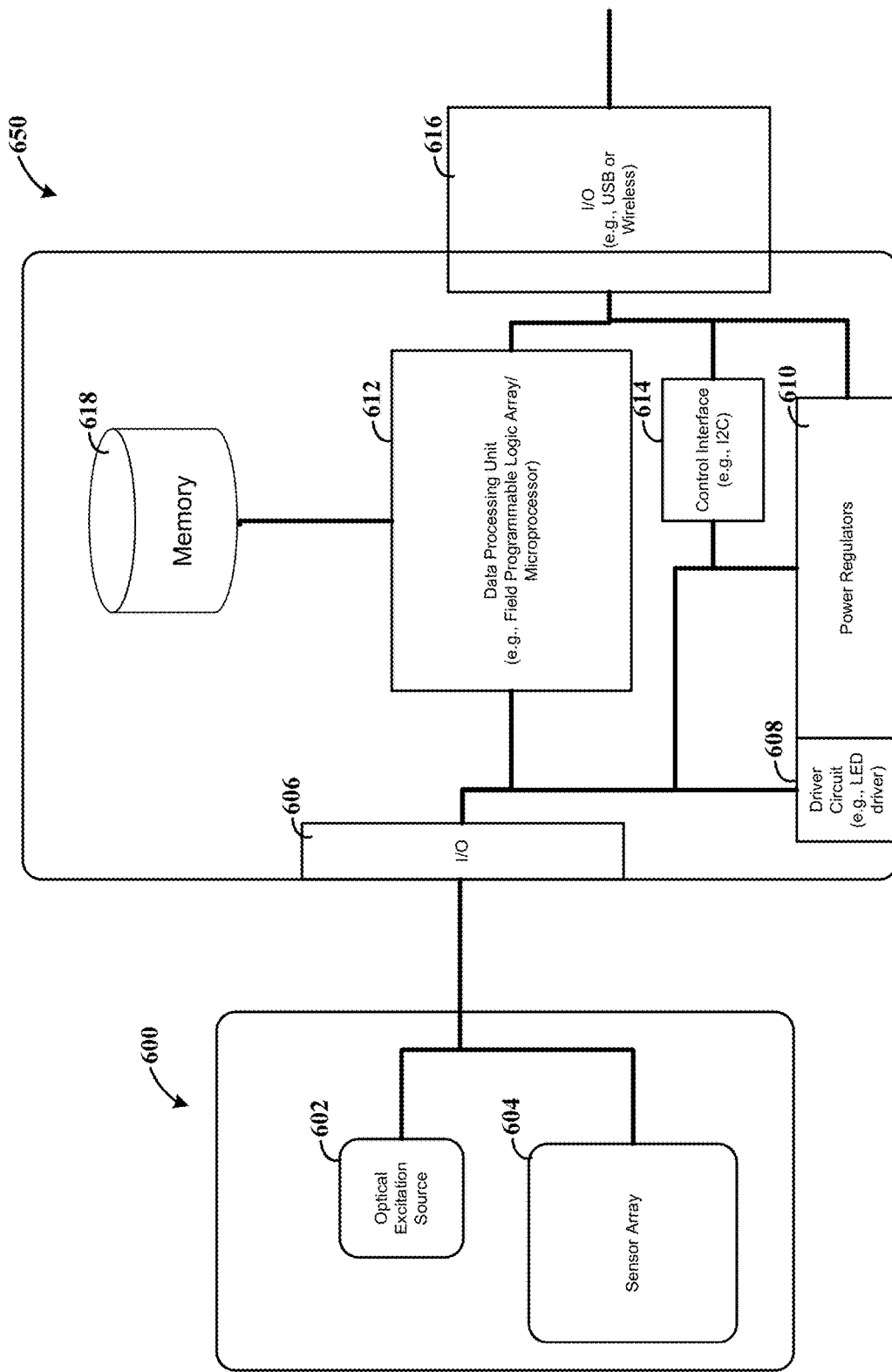
FIG. 6 depicts a block diagram for a microscope system, consistent with an embodiment of the present disclosure.

FIG. 6 depicts a block diagram for a microscope system, consistent with an embodiment of the present disclosure. Two of the electronically active components of the microscope 600 include the optical excitation source 602 and the sensor array 604. In certain embodiments, the microscope 600 receives power and control signals from an external interface module 650. This allows various circuits and components (e.g., power supply, memory storage and/or image processing) to be located remote from the microscope. Interface module 650 can be designed to function as a stand-alone component or for connection with another device, such as a computer.

In certain embodiments, interface module 650 is configured to provide microscope data acquisition and control and is external to the microscope imaging device. In another embodiments, interface module 650 (with or without input/output (I/O) interface 616) can be integrated with the microscope device 600, e.g., for applications where the weight/size does not preclude such integration.

According to one embodiment of the present disclosure, the interface module 650 includes an input/output (I/O) interface 606 (a transmitter/receiver/transceiver circuit). This I/O interface 606 can be used to provide power, control and to transmit image data to and from the microscope 600. For instance, power can be provided from one or more power regulators 610; control signals can be provided from a control interface 614; driver signals 608 for powering the optical excitation source 602; and image data can be communicated to an (image) data processing unit or circuit 612.

Accordingly, microscope 600 can also be configured with one or more transmitter/receiver/transceiver circuits to allow for communication with the interface module 650.

In one embodiment of the present disclosure, I/O interface 606 is connected to the microscope 600 using wired connections. The wired connections can transmit power and communication signals using any number of different protocols. Particular applications (e.g., in vivo imaging of active organisms) benefit from the wired connection being light, flexible and otherwise amenable to movement by the object of the imaging. Thus, certain embodiments implement communication protocols and solutions with low pin/wire counts.

Consistent with other embodiments of the present disclosure, I/O interface 606 is designed to use wireless communications. Wireless control of the microscopy imaging device and wireless data transfer can be particularly useful when several moving imaging objects are being imaged in parallel in sufficiently close proximity to each other. In one, non-limiting, instance, I/O interface 606 can use magnetic field induction, such as near-field communications derived from ISO/IEC 14443. Near-field communications also allow for power to be provided to the microscope wirelessly, e.g., through inductive coupling. Other wireless communication protocols and solutions are also possible.

Consistent with various embodiments, the interface module 650 is designed with an input/output (I/O) interface 616 that interfaces with another device, such as a laptop/desktop computer. This I/O interface 616 could also include a display screen for presenting images captured from microscope 600. Consistent with certain embodiments, I/O interface 616 can be integrated as part of the interface module 650 or a separate component (e.g., connected via wired or wireless communication links).

The various examples discussed herein for the I/O interfaces 606 and 616 are not limiting. The I/O interfaces can be custom designed or implemented consistent with existing communication protocols.

In certain embodiments, memory 618 can be used to store image data and/or software instructions for execution by data processing unit or circuit 612, which can be implemented using specialized processor (e.g., field programmable gate arrays) or general purpose microprocessors configured to execute the specialized software instructions. The memory 618 can include circuits providing non-volatile memory (e.g., flash) and/or volatile memory (e.g., volatile random access memory (RAM)).

A specific embodiment of the present disclosure is implemented using two printed circuit boards (PCBs) that are contained within the microscope 600. The first PCB 602 includes a light emitting diode (LED). The second PCB 604 includes a complementary metal-oxide semiconductor (CMOS) imaging/camera chip. These PCBs are both connected to a custom external system 650 via nine thin and flexible wires (2 wires to the LED PCB 602 and 7 to the camera PCB 604) that are encased in a single polyvinyl chloride (PVC) sheath of outer diameter 1.5 mm. The external system 650 interfaces with a computer via a general-purpose USB imaging data acquisition adapter. This configuration can be particularly useful for enabling real-time microscope control and data acquisition as well as immediate display of images.

An Inter-Integrated Circuit (I2C) serial communication interface is provided using an I2C controller 614. The I2C interface can be used to control the operation and function of the (CMOS) imaging/camera chip that is part of PCB 604. The image data output from the imaging/camera chip is serialized and transmitted according to a digital low-voltage differential swing (LVDS) format.

Consistent with the various embodiments discussed herein, experimental fluorescence microscopes can be fabricated, assembled, and tested. The microscope fabrication, assembly, and testing processes can be implemented in a distributed and streamlined manner. Camera and LED PCBs can be fabricated separately, while lenses and filters are produced or procured independently. The microscope housing can be fabricated as a kit of individual parts to facilitate manufacturing thereof.

With or without imaging optics, the camera PCB can be tested for power, camera control, and the presence of valid output data. Testing of the LED PCB can include the driving of the LED while illumination output is monitored. Once fully assembled, the microscope housing is designed to maintain the optical parts in alignment with the LED and camera PCBs. The microscope housing was made of black Polyetheretherketone (PEEK), which is lightweight, chemically resistant, stiff, and machinable. Although the black housing absorbed the majority of stray light, a thin layer of black felt or other absorbent material can be affixed (e.g., glued) in locations prone to light reflection. A threaded interface between the part of the housing holding the camera PCB and the microscope body is configured to provide fine adjustment of the spacing between the two for setting the specimen plane that is in focus in the acquired image. The modular nature of the microscope design permits removing and interchanging various parts as required, for example, camera and LED PCBs and the filter and dichroic set.

Experimental microscopes manufactured consistent with this method were tested for a variety of features. Table 2 depicts various specifications for the experimentally-fabricated miniature fluorescence microscope used for in vivo imaging of a brain for an active mouse and without image alignment.

TABLE 2

| | |
|---|---|
| Dimensions | 8.4 × 13 × 22 mm$^3$ |
| Mass | 2 g |
| Resolution | 2.5 µm |
| Field-of-view | 0.48 mm$^2$ |
| Photon flux | 3 × 10$^{11}$ ph/cm$^2$/s |
| SNR | 37 dB |
| Imaging duration | 40-50 mins |

Simulated microscope resolution, based on the modulation transfer function (MTF) of the microscope, was determined to be 2.3 Measured microscope resolution, as stated in Table 2 above, was empirically estimated to be approximately 2.5 Microscope resolution was measured by imaging a Siemens Star resolution test pattern.

In order to test the resolution capabilities of the experimental microscope, a sharp edge, a slanted bar, was used as the synthetic scene and imaged with the virtual microscope. The average edge response, or line spread function, was then derived at different cross-sections of the digital image of the slanted bar and the MTF was then calculated. The results support that the Nyquist rate, as determined by the camera pixel pitch, was found to be 89 cycles/mm. This corresponds to a 2.2 µm feature size in the specimen plane. The MTF10, that is, the resolution at which the contrast degrades to 10% of the ideal contrast was shown to be 2.3 µm.

A number of variations are possible from the expressly-discussed embodiments of the present disclosure. For instance, the microscope can be configured to include a local power supply, such as a battery. In other instances, an array of microscopes can be arranged to capture respective images of target objects.

Particular embodiments relate to in vivo imaging of an organism. Various embodiments discussed hereafter relate to the imaging of cerebellar vermis to study microcirculation concurrently with locomotive, and other mouse behaviors, by mounting of an integrated microscope on the cranium. Notwithstanding, the present disclosure is not so limited and can be applied to a variety of different fields and applications.

In particular experimental embodiments relating to in vivo imaging, brain imaging, with the miniature microscope fixed over the mouse brain (in multiple experiments), was implemented once for a mouse exhibiting vigorous locomotor activity. The microscope was attached while the mouse was anesthetized and imaging commenced about 15-60 min after removal from the anesthesia. Using the cranially-attached microscope, multiple video clips of mouse behavior and the correlated microcirculation in the vermis can be captured for various behaviors. For instance, the mouse walking about the behavioral arena represents a first behavior, while the mouse running on an exercise wheel represents a second behavior. In an experimental implementation, microcirculation was recorded using the integrated microscope that captured images at 100 Hz following an intravenous injection of FITC-dextran. This fluorescent dye labeled the blood plasma, allowing erythrocytes to be seen in dark relief. Individual erythrocytes were witnessed flowing through the capillaries. To reduce the possibility of photo-induced alterations in physiology, the duration and mean power of continuous illumination was limited to <5 min and <600 µW for each imaging session. At least 2 min were allowed to elapse between imaging sessions, and the total imaging duration over the course of an experiment was generally around 45 min. Frame acquisition rates were around 100 Hz for the cerebellar vasculature and microcirculation imaging experiments, and 30-46 Hz for Calcium imaging studies.

Although several in vivo applications are discussed herein, the devices and methods of the present disclosure can be used for other imaging solutions, such as morphology determinations, drug screening and other applications.

Consistent with one embodiment, the use of integrated microscopes discussed herein facilitates the identification of phenotypes for various organisms. This is facilitated by the high-resolution imaging that can be used to identify distinguishing characteristics. For instance, phenotypes can be identified for wild-type and erbb3 mutant zebrafish with fluorescence immunolabeling of myelin basic protein with Alexa-488. The spinal cords and posterior lateral nerve can be imaged and used to distinguish in wild-type fish. In erbb3 fish Schwann cells fail to develop the posterior lateral nerve.

Consistent with another embodiment, the use of integrated microscopes facilitates accurate cell counting assays in well plates. For instance, a base concentration (CO≈4.0× 105 cells/mL) of live MCF7 human breast cancer cells labeled with carboxyfluorescein can be diluted, with 8 sample wells for each of 6 concentrations. Optionally, an automated algorithm can be used to provide for fast and efficient counting of cells in the images.

Consistent with one embodiment, the automated algorithm uses successive stages of analysis within a custom cell counting algorithm. A logic circuit such as a (computer) processor circuit (e.g., including a memory circuit/medium for providing the process instructions) performs contrast equalization on (raw) fluorescence image of live MCF7 human breast cancer cells labeled with carboxyfluorescein. The processor circuit next converts the resulting image to binary format, to which an initial segmentation is performed. Single cells are then identified and counted. Iterative rounds of morphological filtering allow segmentation of the clusters of multiple cells that remained after the initial segmentation into individual cells.

Embodiments of the present disclosure are directed toward using a microscopy imaging device as part of a larger optical system. For instance, a microscopy imaging device can be embedded in vivo to facilitate long-term, chronic imaging. This can be facilitated by providing mobile power sources and control/processing circuitry. These and other elements can be integrated within the housing of the microscopy imaging device or connected externally (e.g., using a wired connection to a control unit located elsewhere on the subject). In another instance, a microscopy imaging device can be used in connection with specialized optical devices, for example, to facilitate in vivo endoscopy or to monitor the subject during surgical procedures.

The various embodiments described above and shown in the figures are provided by way of illustration only and should not be construed to limit the disclosure. Based on the above discussion and illustrations, those skilled in the art will readily recognize that various modifications and changes may be made to the present disclosure without strictly following the exemplary embodiments and applications illustrated and described herein. For instance, applications other than in vivo imaging may be amenable to implementation using similar approaches. In addition, one or more of the above example embodiments and implementations may be implemented with a variety of approaches, including digital and/or analog circuitry and/or software-based approaches. These approaches are implemented in connection with various example embodiments of the present disclosure. Such modifications and changes do not depart from the true scope of the present disclosure, including that set forth in the following claims.

As discussed above, specific applications and background details relative to the present disclosure are discussed above, in the description below and throughout the references cited herein. The embodiments in the Appendices may be implemented in connection with one or more of the above-described embodiments and implementations, as well as with those shown in the figures and described below. Reference may be made to the Appendices filed in the underlying provisional application, which are fully incorporated herein by reference.

What is claimed is:
1. An imaging device comprising:
a portable housing that is less than a cubic inch in size, the portable housing containing:
an excitation source configured to provide excitation light,
an optical pathway comprising a first end and a second end;
an objective lens disposed adjacent to the first end;
one or more emission elements configured and arranged to provide a focal plane adjacent to the second end from epifluorescent emission light received from the objective lens; and
an array of optical sensors positioned at the focal plane and configured and arranged to capture an image of a target object from the epifluorescent emission light, wherein the portable housing comprises a modular design that permits individual components to be replaced.

* * * * *